United States Patent [19]

Krieg et al.

[11] Patent Number: 5,405,014
[45] Date of Patent: Apr. 11, 1995

[54] METHOD AND DEVICE FOR THE DETECTION AND IDENTIFICATION OF HARMFUL SUBSTANCES IN BEVERAGE BOTTLES IN FILLING LINES

[75] Inventors: Gunther Krieg, Im Rennich 12, 7500 Karlsruhe 41; Karl Koukolitschek, Karlsruhe; Wilfried Maier, Sulzfeld, all of Germany

[73] Assignee: Gunther Krieg, Karlsruhe, Germany

[21] Appl. No.: 5,352

[22] Filed: Jan. 19, 1993

[30] Foreign Application Priority Data

Jan. 16, 1992 [DE] Germany ............... 42 00 971.5

[51] Int. Cl.6 ............................................. B07C 5/00
[52] U.S. Cl. ........................... 209/524; 209/526; 209/527; 209/577; 209/578
[58] Field of Search ............... 209/3.2, 3.1, 524, 523, 209/522, 526, 527, 577, 576, 578; 198/377, 378

[56] References Cited

U.S. PATENT DOCUMENTS

| | | | |
|---|---|---|---|
| 3,409,128 | 11/1968 | Hutaff | 209/522 |
| 3,601,616 | 8/1971 | Katsumata | . |
| 3,917,947 | 11/1975 | Fenton | 209/524 X |
| 4,108,762 | 8/1978 | Babunovic et al. | 209/524 |
| 4,284,353 | 8/1981 | Yoshida et al. | 209/524 X |
| 4,300,689 | 11/1981 | Franklin et al. | 209/524 |
| 4,368,980 | 1/1983 | Aldred et al. | 209/524 X |
| 4,492,475 | 1/1985 | Takahashi | . |
| 4,551,627 | 11/1985 | Reich | . |
| 4,804,273 | 1/1989 | Tondello et al. | . |
| 4,858,768 | 8/1989 | Plester | 209/3.1 |
| 4,929,828 | 5/1990 | Claypool | 209/524 X |

FOREIGN PATENT DOCUMENTS

| | | |
|---|---|---|
| 2308910 | 2/1973 | Germany . |
| 3233919 | 9/1982 | Germany . |
| 3245908 | 12/1982 | Germany . |
| 4121429 | 6/1991 | Germany . |
| 1422129 | 1/1976 | United Kingdom . |

*Primary Examiner*—David H. Bollinger
*Attorney, Agent, or Firm*—Antonelli, Terry, Stout & Kraus

[57] ABSTRACT

A method and device for detection and identification of liquid, solid, and gaseous foreign substances of beverages and/or beverage residues in re-usable bottles, especially in plastic bottles and other containers. Electromagnetic radiation traverses the walls of the bottles and containers at least once, and by areas of residual liquid, areas with liquid films, solid films on the inside wall and areas with contamination inside the wall are detected by the electromagnetic radiation.

16 Claims, 3 Drawing Sheets

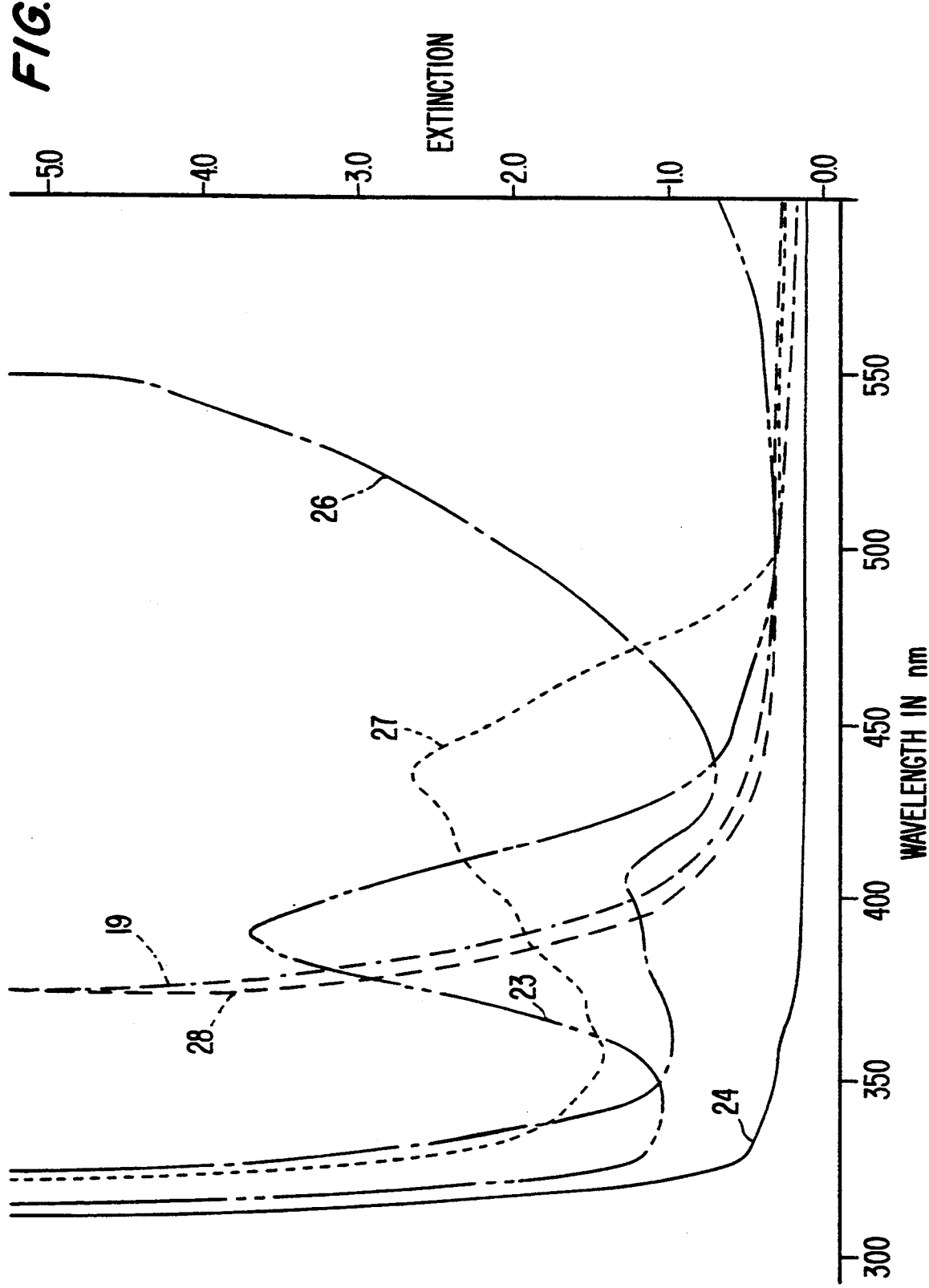

METHOD AND DEVICE FOR THE DETECTION AND IDENTIFICATION OF HARMFUL SUBSTANCES IN BEVERAGE BOTTLES IN FILLING LINES

FIELD OF THE INVENTION

The present invention relates to a method and device for detecting and identifying harmful substances in reuseable bottles or containers for liquid, solid and gaseous containments.

BACKGROUND OF THE INVENTION

The testing of reusable bottles and reusable containers for liquid, solid, and gaseous contaminants is an important technical problem, especially since the introduction of plastic bottles and plastic containers, since the harmful substances such as poisons diffuse into the wall material and, upon refilling with the product in question, for example lemonade, cola, fruit juice, etc., have an adverse affect on the taste.

In German P 41 21 429.3, an efficient method and devices are proposed for solving the problem of harmful substances by using gas samples drawn from the bottle or the container above the level of the liquid. One disadvantage of this approach resides in the fact that materials with extremely low partial pressures, such as, for example, high-boiling vegetable oils, hydraulic oils, inks, water-soluble dyes, naphthalene, etc. cannot be detected reliably if at all.

In U.S. Pat. No. 4,858,768, a method is proposed for investigating, in detail, a liquid drawn from the bottle or container to determine whether the liquid corresponds to the original product in the bottle or container and, if not, rejecting the bottle or container from the refilling process. This is uneconomical since re-usable bottles and containers very rarely return with original product to the filling plant. Consequently, a number of bottles are unjustifiably rejected because many fermentation products, rinsing with water by the consumer, drying out, etc alter the composition of the original product but would not cause the bottle or container to be termed contaminated. In addition, the sole examination of the residual fluid or residue contained in the bottle or container as intended in U.S. Pat. No. 4,858,768 does not solve the problem since harmful substances adsorbed in the walls of the bottle or container would not be detected.

SUMMARY OF THE INVENTION

The aim of the present invention is to provide both a method and a device which, in addition to contaminant analysis in the respective residual fluid, conducts the same analysis on the wall of the bottle or container as well as in a gas chamber of the bottle or container. In addition, the method according to the invention permits a harmful-substance analysis of liquid films located on the wall, for example oil films, films of cleaning agents, detergents, etc., as well as a harmful-substance analysis of the dried product, in other words, the product film, as well as solid films for example thin layers of inks, paints, adhesives, waxes, cosmetic products, etc.

According to the invention, the bottle or container to be investigated is irradiated with electromagnetic radiation of a suitable wavelength, within the total interval between the wavelengths of 200 nm and 10 cm. The wavelength ranges were selected to ensure high permeability of the bottle wall to electromagnetic radiation. The direction of the electromagnetic radiation is adjusted according to the invention in such fashion that both the bottom of the bottle or container as well as the walls of the bottle or container are traversed by the electromagnetic radiation. From the wavelength dependence of the attenuation of the electromagnetic radiation, with consideration according to the invention of the electromagnetic radiation transmission in the material composing the wall of the bottle or container, the respective contaminant in the residual fluid and/or in the gas chamber is detected and analyzed on line. Furthermore, it is simultaneously determined according to the invention, what product was originally used to fill the container or bottle.

BRIEF DESCRIPTION OF THE DRAWINGS

The present invention will now be described in greater detail with reference to the accompanying drawings, wherein.

DETAILED DESCRIPTION

Figure 1:
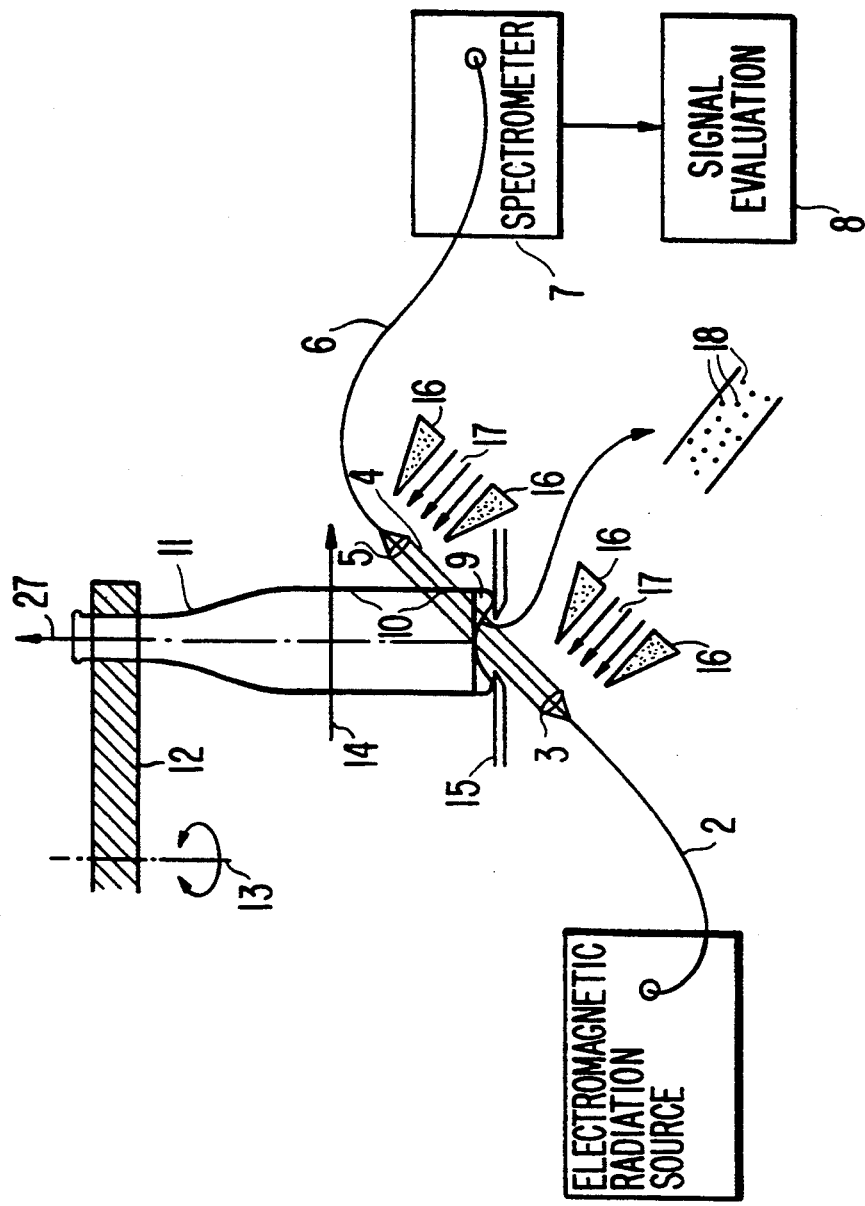
FIG. 1 is a schematic view of an overall arrangement for harmful-substance detection and real-time harmful-substance analysis of residual fluid in a wall of a bottle or container and analysis of liquid solid films on an inside wall of the container in a system in accordance with the present invention.

Referring now to the drawings and, more particularly, to FIG. 1, according to this figure a bottle or container 11 is advanced by a transport device 12 in a filling line. The transport device is adapted to execute a rotational movement around an axis 13 or any other movement, for example, a linear movement. Alternatively, a guide surface 15, which, in the embodiment of FIG. 1 is stationary, may serve as a conveyor belt for transporting bottles or containers.

A real-time material analysis is accomplished by an on-line spectrometer 7 for electromagnetic radiation with a downstream signal evaluation unit 8. Both the spectrometer 7 and signal evaluation unit 8 are described in detail in P 41 21 429.3 with regard to both their construction and their function. The on-line spectrometer 7 is preferably designed for an ultraviolet/visible region and/or for a near and/or medium infrared region of the electromagnetic spectrum. A source 1 generated electromagnetic radiation and transmits the radiation energy through a fiber bundle 2 of quartz glass or of infrared-transparent fluorine-special compounds to a focusing element or lens 3. The lens 3 generates an approximately parallel beam 4 that traverses the bottle or container 11 in a vicinity of a champagne bottom and is focused by a focusing element or lens 5 on a second fiber bundle 6 to reach an input of the on-line spectrometer 7.

Alternatively, a second system may be installed along a line 14 or along other directions not shown in FIG. 1. In a preferred embodiment, the beam direction may also run along a line 27. The entire system according to FIG. 1, in addition to real-time analysis of the residual fluid 9 contained in the bottle or container 11 may be used especially for real-time analysis or liquid/solid films 10 on an interior or inside wall of the bottle or container 11. Additionally, molecules of harmful substances 18, deposited by fusion processes in the wall of the bottle or container 11, are identified.

In order to obtain the largest possible amount of residual fluid in the investigation area, provision can advantageously be made for the bottle or container 11 to be tilted slightly up to a maximum of 45°. This may be performed by a suitable construction of a holder on a transport device 12 engageable with a neck of the bottle or container 11.

In order to avoid contamination during the rough operation to which the focusing elements or lens 3, 5 are necessarily exposed, the focusing elements or lens 3, 5 are flushed by nozzles 16 which deliver a jet of clean air 17. As a result, the condensation of harmful substances, deposition of dust particles, and condensation of water vapor on the focusing element or lens 3, 5 and other components is prevented.

Figure 2B:
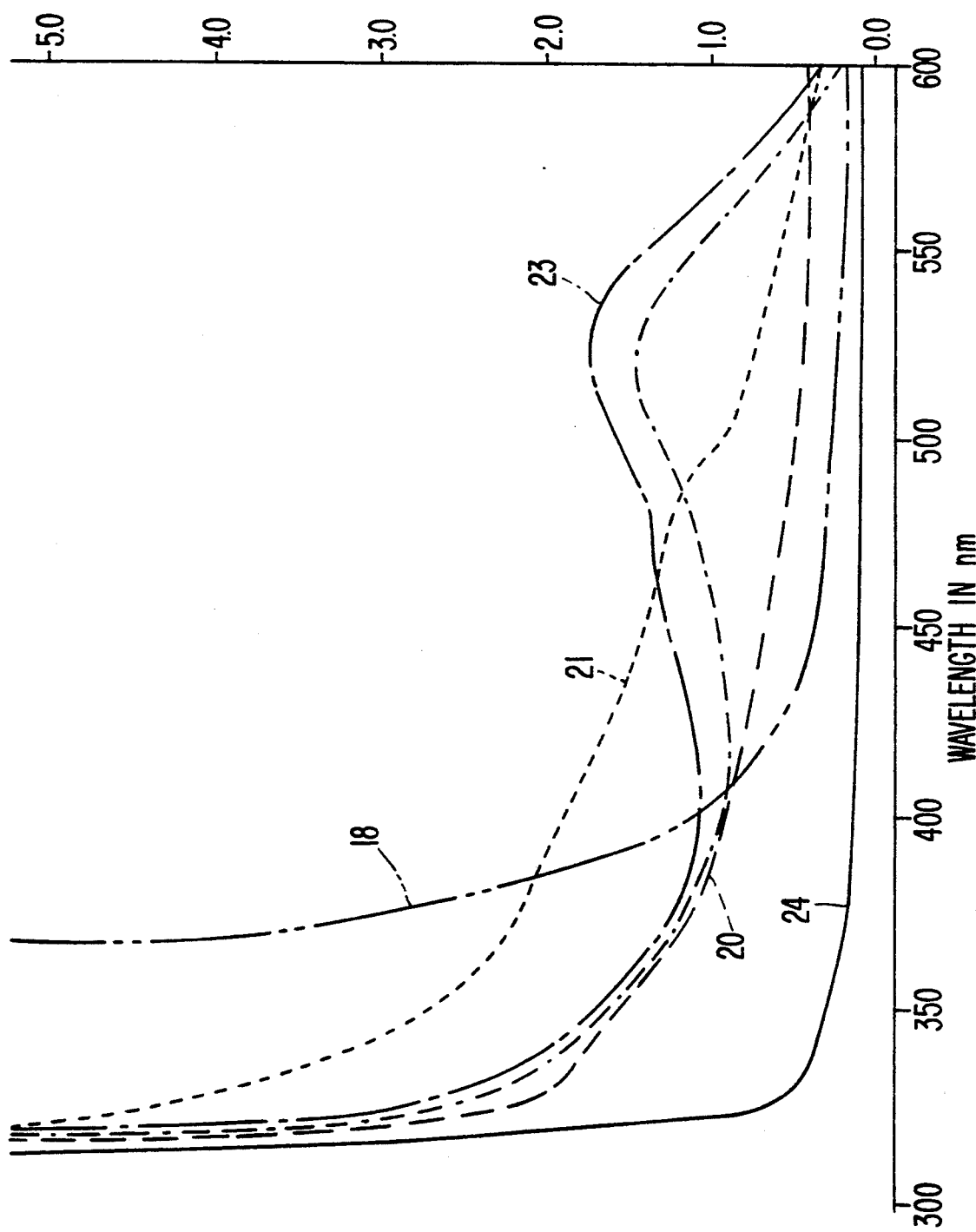
FIG. 2 is a graphical illustration of results of a real-time harmful-substance analysis and/or real-time residual-product analysis in reusable polyethylene beverage bottles.

The results of the real-time analysis according to the invention using the complete system shown in FIG. 1 are shown in FIGS. 2a, 2b, with FIG. 2a depicting wavelength dependencies of the logarithmic attenuation, the so-called extinction E of the electromagnetic radiation for a new uncontaminated bottle or container 24 as well as for dangerous or undesirable contaminations of residual fluid 9 with harmful substances. The wall of the bottle or container 11 and harmful substance films 10 are plotted. Harmful substances shown include a nickel bath galvanic solution 23, ink 26, urine 19, gentle-purpose cleaners 27, and a disinfectant NaCLo 28 as examples.

The typical functional curves for each substance, obtained using the signal evaluation 8, permit clear detection and identification of the harmful substances and especially the functions appropriately plotted in FIG. 2b as well for foodstuffs such as cola 20, strawberry juice 22, orange lemonade 21, vegetable oil 18, and currant juice 23. The clearly characteristic function curves for each substance permit selective determination of the individual substances, in other words, a distinction between poisonous, undesirable, and desirable substances and their concentrations, even when several poisons or poisons and foods are present in a mixture. If mineral water bottles are investigated, only those bottles are considered good that contain water exclusively as a residual liquid, and, for all other residual liquids, including juices, lemonade, or the like, rejection is performed since such contents, even after cleaning of the bottles or containers, can cause an aftertaste in bottles or containers that are refilled with mineral water.

This evaluation and/or analysis is performed on the basis of the functions shown in FIGS. 2a and 2b (18, 19, 20, 21, 22, 23, 24) by a mathematical superimposition of this function on the respective result function obtained according to FIG. 1 from the system.

Conventional methods are utilized for the purpose of performing the evaluation and/or analysis on the basis of the function shown in FIG. 2, in other words, the result function E is determined in accordance with the following relationship:

$$E(\lambda) = a_1 E_1(\lambda) + a_2 E_2(\lambda) + \ldots + a_n E_n(\lambda),$$

where $(\lambda)$ = the wavelength,
$E_1(\lambda)$ = the functional curve for the substance, and
$A_1$ = parameters providing concentration values for the respective substances.

We claim:

1. A method for determining a presence of harmful substances in a form of at least one of a residual liquid, a liquid film and a solid film in used re-useable bottles and containers having a concave bottom portion defining an investigation area of the bottles and containers, the method comprising the steps of:
   conveying the bottles and containers in filling lines through an inspection area,
   subjecting the bottles and containers to electromagnetic radiation such that the electromagnetic traverses, at least once, walls of the bottle and container in the investigation area of the bottles.
   detecting the presence of harmful substances in the investigation area,
   sorting and discarding the bottles and containers in response to a detection of the presence of harmful substances in the bottles and containers.
   guiding the electromagnetic radiation through the investigation area of the bottles and containers by guide elements, and
   spraying the guide elements with air jets of clean air to prevent contamination of the guide elements.

2. A method according to claim 1, wherein the electromagnetic radiation includes individual wavelength ranges.

3. A method according to claim 1, wherein wavelength ranges of the electromagnetic radiation lie in one of an ultraviolet, a visible, near infrared, and infrared region.

4. A method according to claim 1, wherein the steps of subjecting the bottles and containers to electromagnetic radiation and detecting the presence of harmful substances includes decomposing the electromagnetic radiation with a real-time spectrometer, and calculating a wavelength dependence of an extinction of the electromagnetic radiation with a signal evaluation unit.

5. A method according to claim 1, wherein each substance detected is assigned a function of an extinction of the electromagnetic radiation as a function of a wavelength of the electromagnetic radiation.

6. A method according to claim 1, wherein the step of subjecting the bottles and containers to electromagnetic radiation and detecting the presence of harmful substances comprises identifying and determining concentration of the individual substances by comparing the individual substances with predetermined distinction functions of the respective individual substances.

7. A method according to claim 1, wherein, in a multicomponent mixture, the method further comprises the steps of identifying and determining a concentration of the individual substances in the multicomponent mixture, and superimposing an extinction function of the individual substances.

8. A method according to claim 1, wherein the step of detecting includes supplying the electromagnetic radiation to a detector through flexible waveguides.

9. A device for determining a presence of harmful substances in a form of at least one of a residual liquid, a liquid film and a solid film in used reuseable bottles and containers, the device comprising:
   a conveyor adapted to transport the bottles and containers, through an inspection area,
   an electromagnetic radiation source adapted to subject the bottles and containers to electromagnetic radiation such that the electromagnetic radiation traverses, at least once, walls of the bottles and containers in an investigation area of the bottles and containers, a detector cooperable with the electromagnetic radiation source adapted to detect the presence of harmful substances in the investigation area, guide elements adapted to guide the electromagnetic radiation to the investigation area of the bottles and containers, a sprayer adapted to supply air jets of clean air so as to flush the guide elements of contaminants, and wherein the bottles and containers are sorted and discarded by the conveyor upon a detection of the presence of harmful substances in the investigation area of the bottles and containers.

10. A device according to claim 9, wherein the electromagnetic radiation has individual wavelength ranges.

11. A device according to claim 9, wherein wavelength ranges of electromagnetic radiation lie in one of an ultraviolet, visible, near infrared, and infrared region.

12. A device according to claim 9, wherein the detector includes a real-time spectrometer adapted to decompose the electromagnetic radiation, and wherein an evaluation signal unit is provided for calculating a wavelength dependency of an extinction of the electromagnetic radiation.

13. A device according to claim 12, wherein each substance is assigned a function of the extinction as a function of the wavelength.

14. A device according to claim 12, wherein an identification and concentration determination of each individual substance is accomplished by a comparison with the extinction function.

15. A device according to claim 12, wherein flexible waveguides are provided for supplying the electromagnetic radiation to said real-time spectrometer.

16. A device according to claim 9, wherein one of the residual liquid, the liquid film and solid film is of a multicomponent mixture, and wherein an identification and concentration determination of individual substances of the multicomponent mixture is determined by superimposing extinction functions of the individual substances.

* * * * *